United States Patent
Lim et al.

(10) Patent No.: US 7,697,989 B1
(45) Date of Patent: Apr. 13, 2010

(54) COLLET SPRING FOR HIGH VOLTAGE ELECTRICAL CONTACTS IN ICD HEADERS

(75) Inventors: Wisit Lim, Palmdale, CA (US); Narendra Nayak, Santa Clara, CA (US)

(73) Assignee: Pacesetter, Inc., Sylmar, CA (US)

( * ) Notice: Subject to any disclaimer, the term of this patent is extended or adjusted under 35 U.S.C. 154(b) by 820 days.

(21) Appl. No.: 11/403,248

(22) Filed: Apr. 12, 2006

(51) Int. Cl.
*A61N 1/375* (2006.01)

(52) U.S. Cl. .......................... 607/36; 439/837; 439/843; 439/846; 607/37

(58) Field of Classification Search .................. 607/36; 279/2.02; 385/62; 968/111, 135; 82/155; 53/356; 439/843, 844, 851
See application file for complete search history.

(56) References Cited

U.S. PATENT DOCUMENTS

| | | | |
|---|---|---|---|
| 4,278,093 A | 7/1981 | Lafortune et al. | 128/419 P |
| 4,401,359 A * | 8/1983 | Frelk | 439/846 |
| 4,934,366 A | 6/1990 | Truex et al. | 128/419 P |
| 5,252,090 A | 10/1993 | Giurtino et al. | 439/441 |
| 5,261,395 A | 11/1993 | Oleen et al. | 607/15 |
| 5,489,225 A | 2/1996 | Julian | 439/837 |
| 5,545,188 A | 8/1996 | Bradshaw et al. | 607/37 |
| 5,730,628 A * | 3/1998 | Hawkins | 439/843 |
| 6,273,766 B1 * | 8/2001 | Zennamo et al. | 439/843 |
| 2004/0167582 A1 | 8/2004 | Tvaska et al. | 607/37 |

OTHER PUBLICATIONS

Pritchett, Neal. "Features of the Gold Cup." Not Purfect. Dec. 2006. Dec. 8, 2008. <http://www.notpurfect.com/main/goldcup.htm>. Note: The reference refers to the Colt Gold Cup MKIV Series, 70, which has been in existence since the 1970s.*

* cited by examiner

*Primary Examiner*—Mark W Bockelman
*Assistant Examiner*—Elizabeth K So

(57) ABSTRACT

A connector assembly includes a conductive collet spring with an annular base and integral circumferentially spaced cantilevered generally parallel arms terminating at tip members diametrically spaced closer than the diameter of the base. A conductive housing overlying and electrically and mechanically engaged with the collet spring engageably receives the electrical terminal of a medical stimulating device and includes a distal mounting flange. A non-conductive barrel is fittingly attached to the distal mounting flange of the housing and has an inner bore for receiving a medical electrical lead. A non-conductive header encapsulates the connector assembly, is mounted on the casing, and has a header bore aligned with the inner bore for receiving the medical electrical lead which, when inserted and sufficiently advanced through the header bore, the inner bore, and the annular base, the tip members firmly engage the proximal terminal pin thereof.

4 Claims, 6 Drawing Sheets

COLLET SPRING FOR HIGH VOLTAGE ELECTRICAL CONTACTS IN ICD HEADERS

FIELD OF THE INVENTION

The present invention relates generally to a technique for interconnecting electrical leads and electrical medical devices, and more particularly, for interconnecting implantable electrical leads and implantable medical electrical devices such as implantable cardioverter-defibrillators (ICDs) without requiring currently employed components of a connector block, setscrew, and septum to operate successfully.

BACKGROUND OF THE INVENTION

ICDs are devices which are capable of recognizing ventricular tachycardia or ventricular fibrillation and delivering electrical therapy to terminate such an arrhythmia and may also be used to treat the atria. Advantageously, such devices are relatively small, light-weight and implantable. In order to sense and stimulate the heart, however, such ICDs must be used with an ICD lead—an electrical conductor that carries electrical signals between the heart and the ICD. Advantageously, the ICD lead can be inserted into the heart transvenously through a relatively simple and well-known surgical procedure. Disadvantageously, one end of the lead (sometimes designated herein as the "connecting end") must be electrically and mechanically secured to the ICD in a way that provides for a long-term safe and secure, yet detachable, connection. Those skilled in the art of ICDs have long sought after a simple, yet reliable and safe, technique for making this detachable electrical and mechanical connection between the ICD and the connecting end of the ICD lead.

In order to appreciate the advantages of the present invention, it will help first to have a basic understanding of the manner in which the mechanical and electrical connection functions are carried out in known ICDs. The main components associated with the connection function of known ICDs are shown in FIG. 1. An ICD 10 electrically includes a battery 14 that powers electronic circuitry 12. The ICD electronic circuitry 12 and battery 14 are mechanically housed and hermetically sealed in a suitable housing 16. Typically, this casing 16 is shaped to include a flat side or platform 20 to which a suitable epoxy header 22 can be bonded. At least one feedthru terminal 18, in electrical contact with the electronic circuitry 12, passes through the casing 16 and protrudes out from the platform 20. This feedthru terminal 18 is electrically isolated from the casing 16. A platinum wire 24, or other suitable conductive element, connects the terminal 18 to a conductive connector block 26 that is fitted within the header 22. An ICD lead 28, having a proximal electrode 30, connects to the ICD electronic circuitry by inserting the proximal electrode 30 into a receiving channel 31 of the header 22 until the electrode 30 is in contact with the connector block 26. A set screw 32 is then securely tightened using a torque wrench 34 to firmly hold the electrode 30 in both mechanical and electrical connection with the connector block 26. A septum 35 is typically placed over the set screw 32 in order to prevent body fluids from seeping through the set screw hole. Further, sealing ribs or ridges 36 on the connecting end of the ICD lead are designed to tightly engage the inside edges of the receiving channel 31 in order to prevent any body fluids from entering into the receiving channel 31 once the connecting end of the lead has been pushed into the header 22.

Typically, known headers 22 are cast in place from epoxy to the platform 20 of the ICD, or a premolded header is bonded to the platform 20 using a suitable sealing and bonding agent. Further, once the electrical connection is made from the terminal post 18 to the connector block 26, and the header 22 is attached to the housing, all remaining voids within the header, not including the receiving channel 31 into which the proximal end of the lead is to be inserted, must be filled with a suitable filler material, such as a two-component epoxy or silicone rubber.

As is evident from the above description, placing a header on an ICD housing is a very labor-intensive process involving many components. What is needed is a simpler manner of lead attachment that provides the requisite mechanical and electrical connection functions using fewer components and less labor yet providing higher reliability. As mentioned above, many known ICDs use a setscrew connector block assembly to make electrical contact between leads and device. The surgeon secures leads in the header by tightening the setscrew(s) with a torque wrench inserted through the septum. The septum is installed over the setscrew in the header to seal the connector block from body fluid. This process of tightening setscrews establishes electrical contact between lead and device and starts delivery of therapy.

Occasionally, the septum gets damaged either by the torque wrench or the setscrew, creating a leak path for body fluid to come in contact with the connector block. This may result in device malfunction and/or connector block corrosion. Additionally, the quality of electrical contact between the lead and device is compromised due to presence of body fluid.

Damage to setscrews is one of the main reasons for field return of devices. In many devices where the cause of failure is indeterminate, the septum is observed to be damaged.

In order to assemble the septum, a cavity is created in the header. The cavity raises the profile of header surfaces. This raised profile tends to rub against body tissue after implant and is a primary source of irritation and patient discomfort.

Low septums, however, are a cause of rejects in manufacturing. In this regard, it is noteworthy to explain that during normal header manufacturing operation, a cylindrical cavity is created in the side of the header and the septum is installed in the cavity such that the top surface of the septum is flush with the rim of the cylindrical cavity. Sometimes the cavity is created excessively deep, with the result that the septum sits low in the cavity. In this case the top surface of the septum lies below the rim of the cylindrical cavity. This condition is known as a low septum and is a cause of rejects.

This is one of the reasons for often low yield of the casting process when manufacturing ICD headers and, frequently, devices require rework on account of this problem. Further, during quality inspection, septums can get damaged due to insertion of torque wrench.

The present invention addresses these and other needs and it was in light of the foregoing that the present invention was conceived and has now been reduced to practice.

SUMMARY

A connector assembly includes a conductive collet spring with an annular base and integral circumferentially spaced cantilevered generally parallel arms extend from the annular base terminating at tip members which are diametrically spaced closer than the diameter of the base. A conductive housing overlying and electrically engaged with the collet spring is connected to the electrical terminal of a medical stimulating device and includes a distal mounting flange. A non-conductive barrel is fittingly attached to the distal mounting flange of the housing and has an inner bore for receiving a medical electrical lead. A non-conductive header encapsulates the connector assembly, is mounted on the casing, and has a header bore aligned with the inner bore for receiving the medical electrical lead which, when inserted and sufficiently advanced through the header bore, the inner bore, and the annular base, the tip members firmly engage the proximal terminal pin thereof and assure electrical continuity with the device's electronic circuitry.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION

Figure 1:
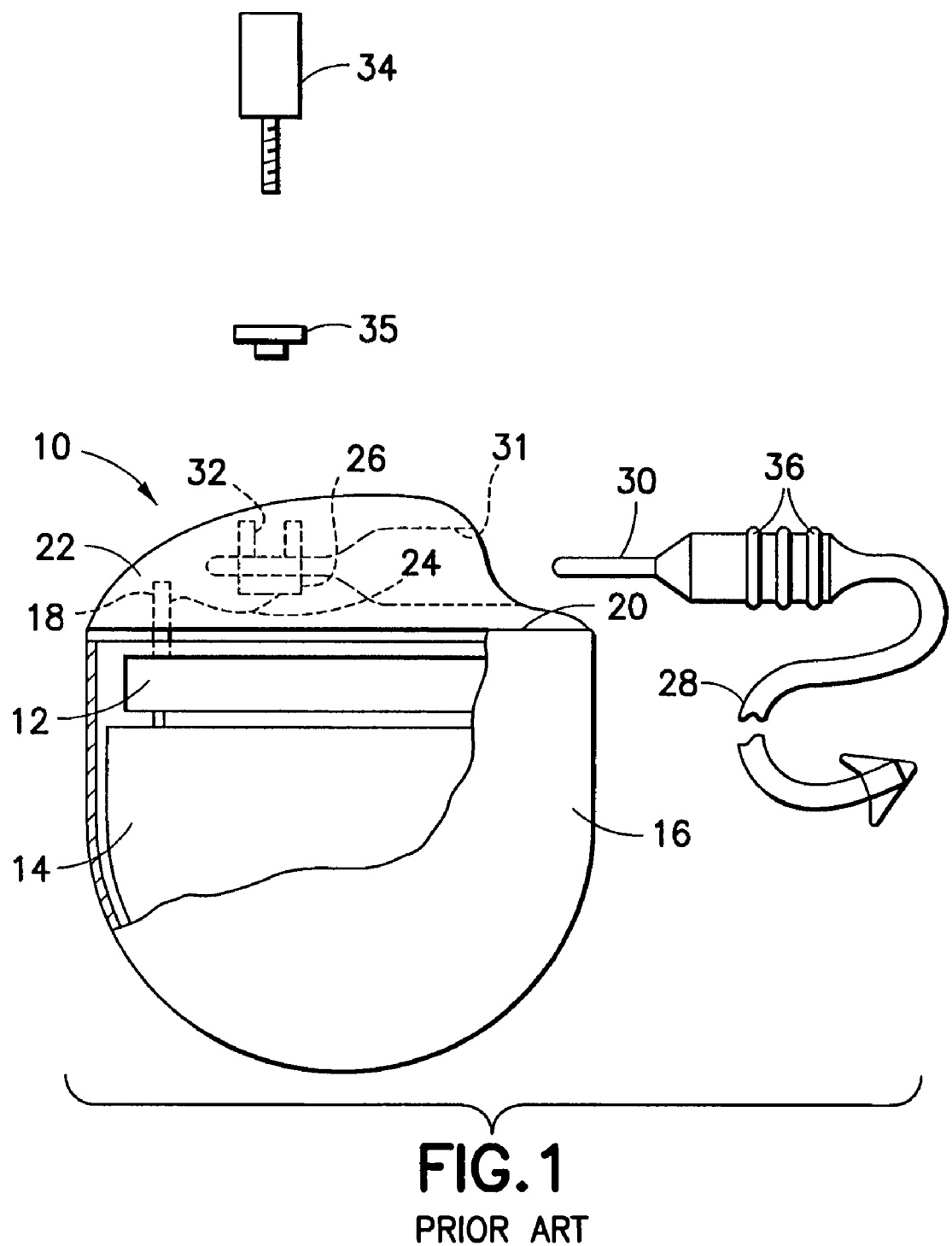
FIG. 1 is an exploded perspective view of a known implantable medical device in the form of an ICD, illustrating a sealed housing, its associated header, and an associated lead ready for insertion into a receiving bore of the header.
Figure 2:
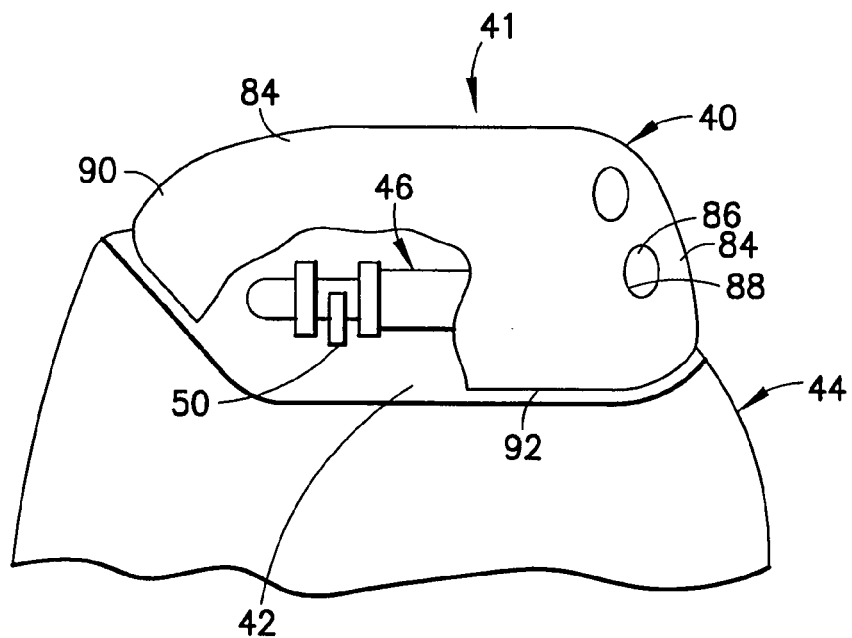
FIG. 2 is a detail perspective view, partially cut away, of an ICD and associated header containing the connector assembly of the invention.
Figure 3:
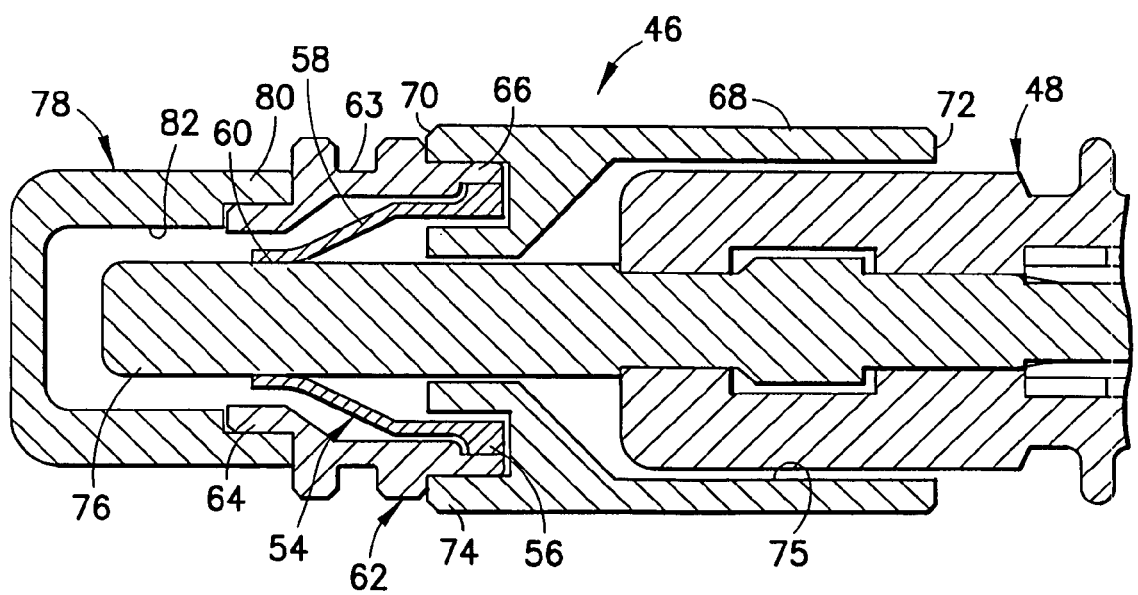
FIG. 3 is a longitudinal cross section view in elevation of the connector assembly of the invention into which a medical electrical lead has been inserted.

Refer again to the drawings and, this time, to FIGS. 2 and 3. FIG. 2 illustrates a detail perspective view of a header assembly 40, embodying the invention, for an ICD 41. The header assembly 40 is shown in position mounted on a mounting surface 42 of a casing 44 of the ICD 41 containing a battery and electronic circuitry, not here shown, but generally provided in the manner illustrated in FIG. 1. FIG. 3 is a longitudinal cross section view in elevation of a connector assembly 46 of which one is seen in FIG. 2 within the header assembly 40 and to which is coupled a body implantable medical electrical or ICD lead 48. Although the present invention will be described with reference to the embodiments shown in the drawings, it should be understood that the present invention can be embodied in many alternate forms or embodiments. In addition, any suitable size, shape or type of elements or materials could be used.

In FIG. 2, an electrical terminal 50 connected to the electronic circuitry within the casing 44 projects out of the mounting surface 42. While only one electrical terminal is shown, there may be several, depending on the specific construction of the ICD 41.

Figure 4:
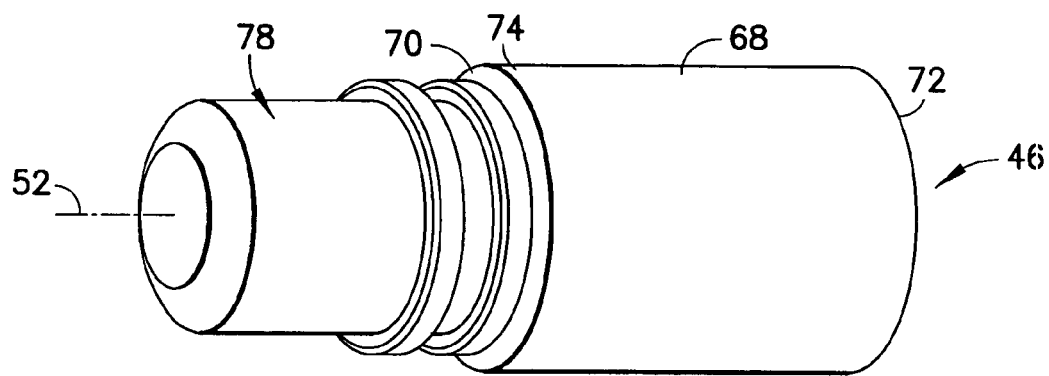
FIG. 4 is a perspective view of the connector assembly of the invention.
Figure 5:
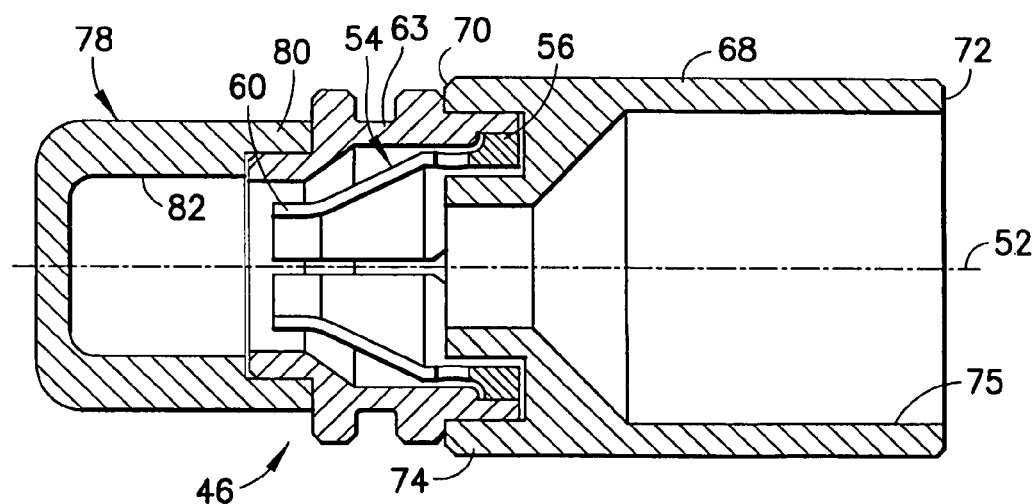
FIG. 5 is a longitudinal cross section view in elevation of the connector assembly of the invention without a medical electrical lead inserted.
Figure 6:
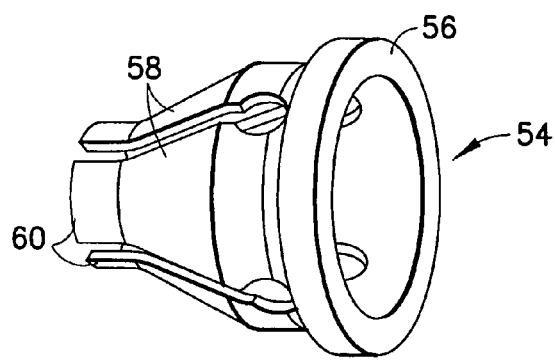
FIG. 6 is a perspective view of a collet spring, one component of the connector assembly of the invention.
Figure 7:
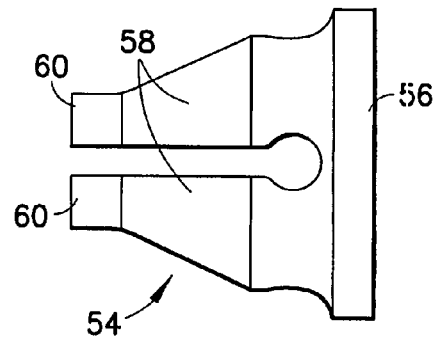
FIG. 7 is a side elevation view of the collet spring.
Figure 8:
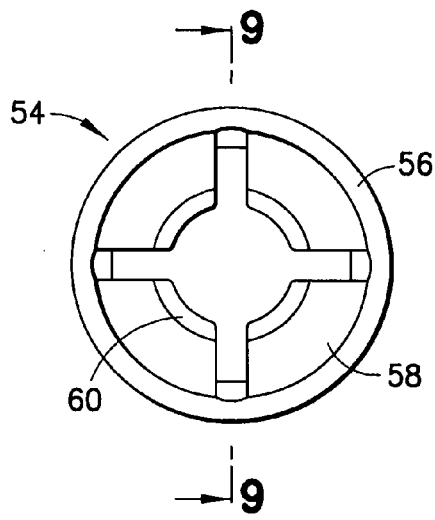
FIG. 8 is an end elevation view of the collet spring.
Figure 9:
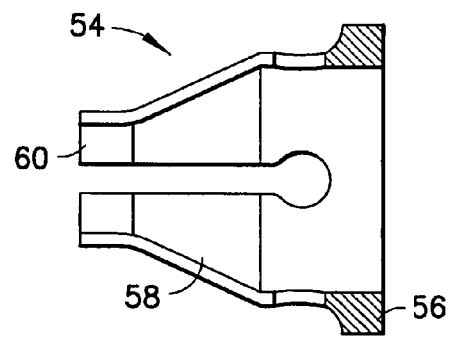
FIG. 9 is a cross section view taken generally along line 9-9 in FIG. 8.
Figure 12:
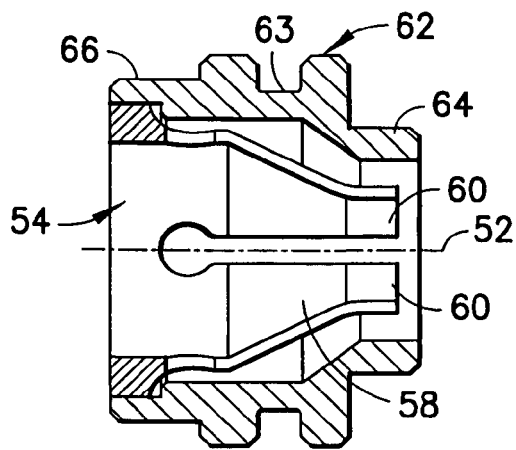
FIG. 12 is a cross section view taken generally along line 12-12 in FIG. 11.
Figure 13:
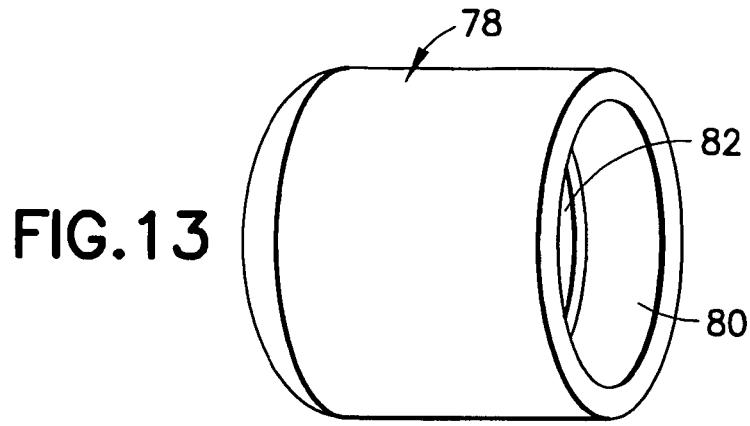
FIG. 13 is a perspective view of an end cap, another component of the connector assembly of the invention.
Figure 14:
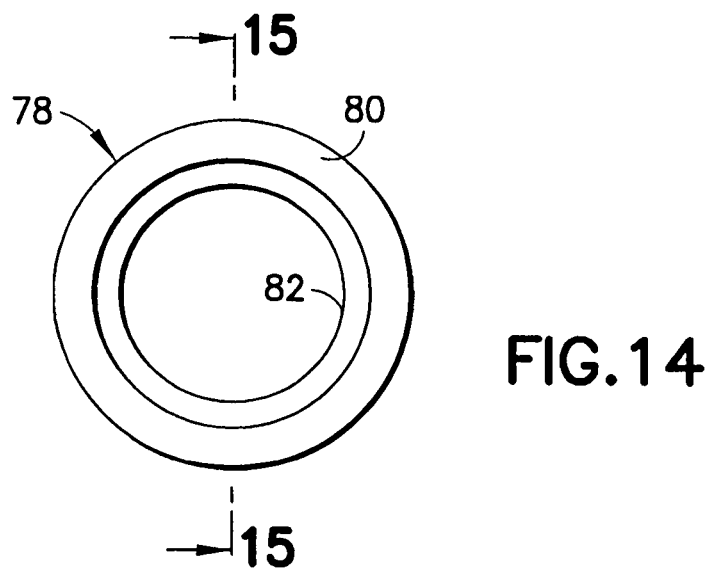
FIG. 14 is an end elevation view of the end cap.
Figure 15:
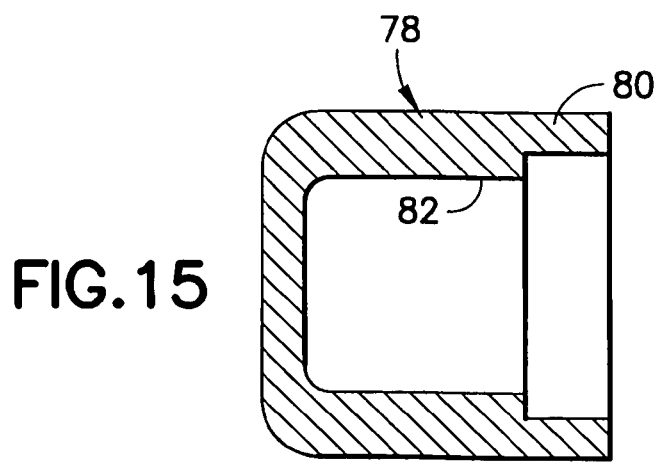
FIG. 15 is a cross section view taken generally along line 15-15 in FIG. 14.

Continuing to view FIG. 3 together with FIGS. 4 and 5, the connector assembly 46 is illustrated in relation to a longitudinal axis 52 and includes an electrically conductive collet spring 54 (FIGS. 3, 5, 6, 7, 8, 9, and 12) composed of a biocompatible metal such as titanium, stainless steel, platinum, or MP35N. Collet spring 54 is constructed with an annular base 56 lying in a plane transverse of the longitudinal axis 52 (FIGS. 4, 5, and 12). A plurality of circumferentially spaced cantilevered arms 58 integral with the annular base 56 extend away from the annular base and are generally parallel to the longitudinal axis 52. Each of the arms 58 terminate at a tip member 60 and the plurality of the tip members 60 are at a uniform radial distance from the longitudinal axis 52 which, as clearly seen in FIGS. 5-9 is less than a radial distance between the annular base 56 and the longitudinal axis 52.

Figure 10:
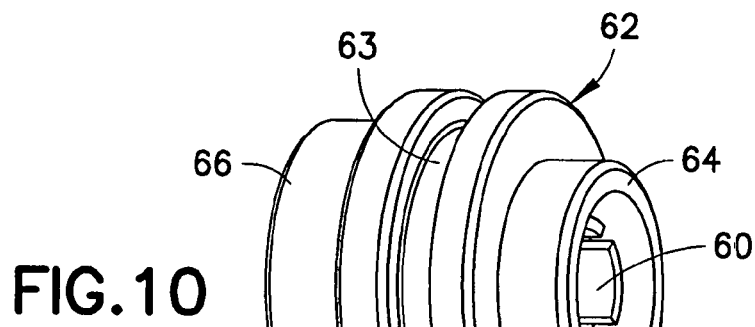
FIG. 10 is a perspective view of a collet spring and housing sub-assembly.
Figure 11:
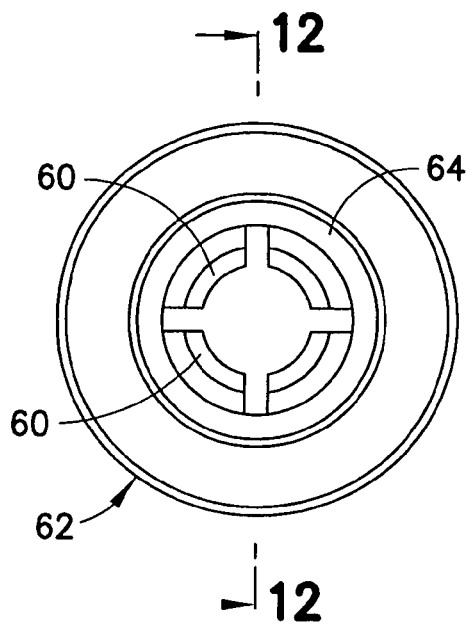
FIG. 11 is an end elevation view of the collet spring and housing sub-assembly.

Turning now especially to FIGS. 10, 11, and 12, an electrically conductive housing 62 overlies, and is mechanically and electrically engaged, as by spot welding, with the collet spring 54. The housing 62 has an annular groove 63 lying in a plane transverse of the longitudinal axis 52 for engageably receiving the electrical terminal 50 (FIG. 2) of the medical stimulating device, or ICD 41. At an appropriate stage of the fabrication of the header assembly 40, the electrical terminal 50 is welded to the groove 63 of the housing 62. The housing 62 extends between a proximal annular mounting flange 64 generally coextensive with the tip members 60 of the collet spring 54 and a distal annular mounting flange 66 generally coextensive with the annular base 56.

A non-conductive barrel member 68 (FIGS. 3, 4, and 5) extends between proximal and distal ends 70, 72, respectively, and is aligned with the longitudinal axis 52. The barrel member 68 has an annular flange 74 at its proximal end 70 and has an inner bore 75 for receiving a proximal terminal pin 76 (FIG. 3) of the medical electrical lead 48. The proximal annular flange 74 is fittingly attached to the distal mounting flange 66 of the housing 62.

A non-conductive end cap 78, as seen especially well in FIGS. 3, 4, 5, 13, 14, and 15, includes an annular mounting flange 80 and has a receptive cavity 82. The mounting flange 80 of the end cap 78 is fittingly attached to the proximal mounting flange 64 of the housing 62 at the receptive cavity to thereby enclose the proximal end of the connector assembly 46.

As seen in FIG. 2, an electrically non-conductive header 84 encapsulates the connector assembly 46 and is mounted on the mounting surface 42 of the casing 44 and has a header bore 86 (FIG. 2) aligned with the inner bore 75 of the barrel member 68. The header bore 86 extends between a bore entrance 88 and the inner bore 75 of the barrel member 68 for receiving the proximal terminal pin 76 of the medical electrical lead 48. With this construction, when the proximal terminal pin 76 of the medical electrical lead 48 is inserted through the header bore 86 and through the inner bore 75 and is sufficiently advanced through the annular base 56 of the collet spring 54, the tip members 60 of the plurality of cantilevered arms 58 firmly engage the proximal terminal pin 76 and assure electrical continuity between the proximal terminal pin and the electronic circuitry of the medical stimulating device, or ICD, 41.

The header 84 may be molded in place on the mounting surface 42 of the casing 44 encapsulating the connector assembly 46 comprised of the end cap 78, the collet spring 54, the housing 62, and the barrel member 68. Alternatively, the header 84 may be pre-molded with an outer peripheral surface 90 and an undersurface 92 for mounting engagement on the mounting surface 42 of the ICD 41. During the procedure of molding the header 84, the end cap 78, the housing 62, and the barrel member 68 protect the interior of the connector assembly 46 against the intrusion of the fluid plastic or epoxy material and also provide for electrical insulation during the operation of the resulting medical stimulating device.

It should be understood that the foregoing description is only illustrative of the invention. Various alternatives and modifications can be devised by those skilled in the art without departing from the invention. For example, although the foregoing description has referred primarily to the application of the invention to a DF-1 lead pin, it can also be beneficially employed with respect to other lead pin designs such as IS-1, IS-4, and DF-4. Accordingly, the present invention is intended to embrace all such alternatives, modifications and variances which fall within the scope of the appended claims.

What is claimed is:

1. An implantable medical device comprising:
    a casing containing electronic circuitry and having a mounting surface and at least one electrical terminal connected to the electronic circuitry and projecting out of the mounting surface; and
    an electrically non-conductive header mounted on the mounting surface of the casing having a header bore with a longitudinal axis and extending between a bore entrance and an inner terminal end for receiving a proximal terminal pin of the medical electrical lead, the electrically non-conductive header comprising:
    an electrically conductive collet spring within the header generally aligned with the longitudinal axis and including an annular base, the collet spring being electrically in contact with the at least one electrical terminal of the medical stimulating device and lying in a plane transverse of the longitudinal axis and a plurality of circumferentially spaced cantilevered arms integral with the annular base and extending away from the annular base in a direction away from the bore entrance and generally parallel to the longitudinal axis, the plurality of arms terminating at tip members, respectively, which are at a uniform radial distance from the longitudinal axis which is less than a radial distance between the annular base and the longitudinal axis;
    an electrically conductive housing overlying and mechanically and electrically engaged with the collet spring, the housing having an annular groove lying in a plane transverse of the longitudinal axis for engageably receiving the at least one electrical terminal of the medical stimulating device; and
    a non-conductive end cap including an annular mounting flange and having a receptive cavity;
    wherein the housing extends between a proximal annular mounting flange generally coextensive with the tip members of the collet spring and a distal annular mounting flange generally coextensive with the annular base of the collet spring;
    wherein the end cap is fittingly attached to the proximal mounting flange at the receptive cavity; and
    wherein the header is molded in place on the mounting surface of the casing and encapsulates the collet spring and the housing.

2. A header assembly as set forth in claim 1 wherein the header is pre-molded and has an outer peripheral surface and an undersurface for mounting engagement on the mounting surface of the medical device.

3. An implantable medical device comprising:
    a casing containing electronic circuitry and having a mounting surface and at least one electrical terminal connected to the electronic circuitry and projecting out of the mounting surface; and
    a connector assembly having a longitudinal axis including:
    an electrically conductive collet spring including an annular base lying in a plane transverse of the longitudinal axis and a plurality of circumferentially spaced cantilevered arms integral with the annular base and extending away from the annular base and in a direction away from the bore entrance and generally parallel to the longitudinal axis, the plurality of arms terminating at tip members, respectively, which are at a uniform radial distance from the longitudinal axis which is less than a radial distance between the annular base and the longitudinal axis;
    an electrically conductive housing overlying and mechanically and electrically engaged with the collet spring, the housing having an annular groove lying in a plane transverse of the longitudinal axis for engageably receiving the at least one electrical terminal of the medical stimulating device, the housing extending between a proximal annular mounting flange generally coextensive with the tip members of the collet spring and a distal annular mounting flange generally coextensive with the annular base;
    a non-conductive barrel member extending between proximal and distal ends aligned with the longitudinal axis, having an annular flange at its proximal end, and having an inner bore for receiving a proximal terminal pin of the medical electrical lead, the proximal annular flange being fittingly attached to the distal mounting flange of the conductive housing;
    an electrically non-conductive header encapsulating the connector assembly and mounted on the mounting surface of the casing and having a header bore aligned with the inner bore of the barrel member and extending between a bore entrance and the inner bore of the barrel member for receiving the proximal terminal pin of the medical electrical lead; and
    a non-conductive end cap including an annular mounting flange and having a receptive cavity;
    wherein, when the proximal terminal pin of the medical electrical lead is inserted through the header bore and through the inner bore and is sufficiently advanced through the annular base, the tip members of the plurality of arms firmly engage the proximal terminal pin and assure electrical continuity between the proximal terminal pin and the electronic circuitry of the medical stimulating device;
    wherein the housing extends between a proximal mounting flange generally coextensive with the tip members of the collet spring and a distal mounting flange generally coextensive with the annular base of the collet spring;
    wherein the end cap is fittingly attached to the proximal mounting flange at the receptive cavity; and
    wherein the header is molded in place on the mounting surface of the casing and encapsulates the collet spring and the housing.

4. A header assembly as set forth in claim 3 wherein the header is pre-molded and has an outer peripheral surface and an undersurface for mounting engagement on the mounting surface of the medical device.

* * * * *